US007790183B2

(12) United States Patent
Darouiche et al.

(10) Patent No.: US 7,790,183 B2
(45) Date of Patent: Sep. 7, 2010

(54) COMBINATION OF ANTIMICROBIAL AGENTS AND BACTERIAL INTERFERENCE TO COAT MEDICAL DEVICES

(75) Inventors: Rabih O. Darouiche, Houston, TX (US); Richard Hull, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 845 days.

(21) Appl. No.: 10/788,060

(22) Filed: Feb. 26, 2004

(65) Prior Publication Data

US 2004/0166094 A1 Aug. 26, 2004

Related U.S. Application Data

(62) Division of application No. 09/877,898, filed on Jun. 8, 2001, now Pat. No. 6,719,991.

(60) Provisional application No. 60/210,715, filed on Jun. 9, 2000.

(51) Int. Cl.
| A61F 13/00 | (2006.01) |
| A61F 2/00 | (2006.01) |
| A01N 63/00 | (2006.01) |
| A61K 39/38 | (2006.01) |
| A61K 39/02 | (2006.01) |
| A61K 9/50 | (2006.01) |
| A61K 39/108 | (2006.01) |
| A61K 39/112 | (2006.01) |
| A61L 33/00 | (2006.01) |

(52) U.S. Cl. ............... 424/234.1; 424/184.1; 424/422; 424/423; 424/241.1; 424/258.1; 424/259.1; 424/93.48; 427/2.1; 427/2.3; 427/2.25; 427/2.28; 427/2.21

(58) Field of Classification Search ............... 424/184.1, 424/234.1
See application file for complete search history.

(56) References Cited

U.S. PATENT DOCUMENTS

| 3,262,864 A | 7/1966 | Kouchner |
| 4,442,133 A | 4/1984 | Greco et al. |
| 4,952,419 A * | 8/1990 | De Leon et al. ............ 427/2.14 |
| 5,089,205 A | 2/1992 | Huang et al. |
| 5,217,493 A | 6/1993 | Raad et al. |
| 5,344,411 A | 9/1994 | Domb et al. |
| 5,498,416 A | 3/1996 | Carsenti et al. |
| 5,616,338 A | 4/1997 | Fox et al. |
| 5,624,704 A | 4/1997 | Darouiche et al. |
| 5,645,830 A | 7/1997 | Reid et al. |
| 5,705,160 A | 1/1998 | Bruce et al. |
| 5,709,857 A | 1/1998 | Morelli et al. |
| 5,716,406 A | 2/1998 | Farber |
| 5,804,179 A | 9/1998 | Bruce et al. |
| 5,853,745 A | 12/1998 | Darouiche |
| 5,902,283 A | 5/1999 | Darouiche |
| 6,004,551 A | 12/1999 | Reid et al. |
| 6,143,037 A | 11/2000 | Goldstein et al. |
| 6,162,487 A | 12/2000 | Darouiche |
| 6,166,007 A | 12/2000 | Sodemann |
| 6,296,863 B1 | 10/2001 | Trogold et al. |
| 6,344,201 B1 | 2/2002 | Maurelli et al. |
| 6,365,220 B1 | 4/2002 | Burrell et al. |
| 6,368,611 B1 | 4/2002 | Whitbourne et al. |
| 6,423,706 B2 | 7/2002 | Sodemann |
| 6,428,491 B1 | 8/2002 | Weiss |
| 6,468,649 B1 | 10/2002 | Zhong |
| 6,498,157 B2 | 12/2002 | Sodemann |
| 6,558,686 B1 | 5/2003 | Darouiche |
| 6,589,591 B1 | 7/2003 | Mansouri et al. |
| 6,719,991 B2 * | 4/2004 | Darouiche et al. ........... 424/422 |
| 7,144,992 B2 * | 12/2006 | Madhyastha ................ 530/400 |
| 7,238,363 B2 * | 7/2007 | Mansouri et al. ............ 424/423 |
| 7,612,045 B2 * | 11/2009 | Eldridge ...................... 514/31 |
| 2002/0031601 A1 * | 3/2002 | Darouiche et al. ........... 427/2.1 |
| 2002/0098278 A1 | 7/2002 | Bates et al. |
| 2002/0120333 A1 | 8/2002 | Keogh et al. |

(Continued)

FOREIGN PATENT DOCUMENTS

EP 0882461 12/1998

(Continued)

OTHER PUBLICATIONS

Schierholz et al, J. Hospital Infection, 2001, 49:87-93.*

(Continued)

*Primary Examiner*—N. M Minnifield
(74) *Attorney, Agent, or Firm*—Fulbright & Jaworski L.L.P.

(57) ABSTRACT

This invention relates to a method for coating a medical device comprising the steps of applying to at least a portion of the surface of said medical device, an antimicrobial coating layer and a non-pathogenic bacterial coating layer, wherein the antimicrobial and non-pathogenic bacterial coating layers inhibit the growth of pathogenic bacterial and fungal organisms. The non-pathogenic bacterium used in the bacterial coating layer is resistant to the antimicrobial agent. Furthermore, the non-pathogenic bacterium layer includes at least one of the following: viable whole cells, non-viable whole cells, or cellular structures or extracts. The antimicrobial agent and non-pathogenic bacterium are used to develop a kit comprising these compositions in one container or in separate containers. The kit is used to coat a catheter prior to implantation in a mammal.

9 Claims, No Drawings

U.S. PATENT DOCUMENTS

| | | | | |
|---|---|---|---|---|
| 2003/0134779 | A1* | 7/2003 | Diarra et al. | 514/6 |
| 2004/0166094 | A1* | 8/2004 | Darouiche et al. | 424/93.4 |
| 2004/0166102 | A1* | 8/2004 | Darouiche et al. | 424/93.45 |
| 2005/0049181 | A1* | 3/2005 | Madhyastha | 514/8 |
| 2006/0246208 | A1* | 11/2006 | Mansouri et al. | 427/2.1 |
| 2009/0016990 | A1* | 1/2009 | Alberte et al. | 424/85.5 |
| 2009/0041727 | A1* | 2/2009 | Suzuki et al. | 424/93.4 |
| 2009/0226541 | A1* | 9/2009 | Scholz et al. | 424/672 |

FOREIGN PATENT DOCUMENTS

| | | |
|---|---|---|
| WO | WO-9911286 | 3/1999 |
| WO | WO-0016624 | 3/2000 |
| WO | WO-0195876 | 12/2001 |

OTHER PUBLICATIONS

Darouiche, Clinical Infectious Diseases, 2001, 33:1567-1572.*
Habash et al, J. Clinical Pharmacology, 1999, 39:887-898.*
Kil et al, J. Clinical Microbiology, Sep. 1997, 35/9:2370-2374.*
Reid, International J. Antimicrobial Agents, 1999, 11:223-226.*
Darouiche et al, J. Infectious Diseases, Oct. 1997, 176/4:1109-1112 abstract only.*
Morck et al, International J. Antimicrobial Agents, Jul. 1994, 4/Supplement 2:S21-S27 abstract only.*
von Eiff et al, Drugs, 2005, 65/2:179-214.*
Raad et al, J. Infectious Diseases, Feb. 1996, 173/2:418-424.*
Trautner et al, Arch. Intern. Med., Apr. 26, 2004, 164:842-850.*
Denton et al, Clinical Microbiology reviews, Jan. 1998, 11/1:57-80.*
Bergogne-Berezin et al, J. Hospital Infection, 1995, 30/Supplement:441-452.*
Grozdanov et al, J. Bacteriology, Aug. 2004, 186/16:5432-5441.*
Paterson, Am. J. Infect. Control, 2006, 34:S20-S28.*
Alekshun et al, Biochemical Pharmacology, 2006, 71:893-900.*
Davison et al, Trends in Microbiology, Dec. 2000, 8/12:554-559.*
Sunde et al, Microbial Drug Resistance, 1998, 4/4:289-299.*
Darouiche et al Urology, 2001, 58:339-344.*
van den Bogaard et al, International J. Antimicrobial Agents, 2000, 14:327-335.*
Caprioli et al, International J. Antimicrobial Agents, 2000, 14:295-301.*
Trautner et al, Urology, 2003, 61:1059-1062.*
Denton, International J. Antimicrobial Agents, 2007, 29/Suppl.*
Vatopoulos et al, J. Hospital Infection, 1996, 34:11-22.*
Kim et al, Foodborne Pathogens and Disease, 2005, 2/4:304-316.*
Creighton, In: Proteins, 1984, pp. 314-315.*
Nosoh et al, Protein Stability and Stabilization Through Protein Engineering 1991, pp. 197-217.*
Creighton, In: Protein Structure a pracital approach, 1989, pp. 184-186.*
Kumar et al, PNAS, USA, Feb. 1990, 87:1337-1341.*
Bowie et al, Science, Mar. 16, 1990, 247:1306-1310.*
Russell, The Lancet, Infectious Diseases, Dec. 2003, 3:794-803.*
Brook, Itzhak, Bacterial Interference, Critical Reviews in Microbiology, 25(3):155-172 (1999).
Hull, Richard A. et al. Virulence Properties of *Escherichia coli* 83972, a Prototype Strain Associated with Asymptomatic Bacteriuria; Infection and Immunity, Jan. 1999, p. 429-432.
Hull, Richard A. et al. Urinary Tract Infection Prophylaxis Using *Escherichia Coli* 83972 in Spinal Cord Injured Patients; The Journal of Urology; vol. 163, 872-877, Mar. 2000.
Solomon, Donald et al. Antibiotic Releasing Polymers; Journal of Controlled Release, 6 (1987) 343-352.
Trauther et al, "Pre-Inoculation of Urinary Catheters with *Escherichia Coli* 83972 Inhibits Catheter Colonization by *Enterococcus faecalis*," The Journal of Urology, 167: 375-379 (Jan. 2002).
Trautner et al, "*Escherichia coli* 83972 Inhibits catheter Adherence by a Broad Spectrum of Uropathogens," Urology 61(5): 1059-1062; 2003.
Reid et al, Clinical Microbiology Reviews, Oct. 1990, 3/4: 335-344.
Raad et al, Antimicrobial Agents & Chemotherapy 39/11: 2397-2400.
Darouiche et al, Antimicrobial Agents & chemotherapy 38/5: 1059-1064.
Pace et al, "Inactivated Whole-Cell Bacterial Vaccines: Current Status and novel Strategies," Vaccine vol. 16, 1998; pp. 1563-1574.
Nayir et al, "The Effects of Vaccination with Inactivated Uropathogenic Bacteria in Recurrent Urinary Tract Infections of Children," Vaccine vol. 13, No. 11, 1995, pp. 987-990.
Agarwal et al., "A new method of detection and differentiation of pathogenic from non-pathogenic Aspergillus species", J Med Microbiol., Jul. 2001, 653-4, vol. 50(7).
Ewald et al., "Micro-Organisms For Education", Department of Biology, The College of William & Mary, May 1997, online <http://www.science-projects.com/safemicrobes.htm>.
Greene et al., "Evaluation of a two-hour method for screening pathogens from stool specimens", J Clin Microbiol., Aug. 1984, 285-287, vol. 20(2).
Haddix et al., "Measurement of Mutation to Antibiotic. Resistance: Ampicillin Resistance. in Serratia marcescens", Bioscene, Feb. 2000, 17-21, vol. 26(1).
Negishi, "Pseudomonas solanacearum: Plasmid pJTPS1 Mediates a Shift from the Pathogenic to Nonpathogenic Phenotype", The American Phytopathological Society, 1993, 203-209, vol. 6(2).
Sambrook et al., "Molecular Cloning: A Laboratory Manual (Second Edition)", book, Cold Spring Harbor Laboratory Press, 1989, 1.3-1.6.
Sansonetti et al., "Involvement of a plasmid in the invasive ability of Shigella flexneri", Infect Immun., Mar. 1982, 852-60, vol. 35(3).
The Office of Biotechnology, Iowa State University, "DNA Transformation Of Bacteria—Ampicillin Resistance", Revised Mar. 2003, online <http://www.biotech.iastate.edu/lab_protocols/DNA_Transformation_Amp.pdf>.
Canadian Office Action issued Jan. 15, 2009, during the prosecution of Canadian Application No. 2,411,944.

* cited by examiner

COMBINATION OF ANTIMICROBIAL AGENTS AND BACTERIAL INTERFERENCE TO COAT MEDICAL DEVICES

This application is a divisional application of application Ser. No. 09/877,898, now U.S. Pat. No. 6,719,991, filed Jun. 8, 2001 which claims priority to Provisional Application No. 60/210,715, which was filed on Jun. 9, 2000.

FIELD OF INVENTION

The present invention relates to a method of coating a medical device with an antimicrobial agent and a non-pathogenic bacterium which is resistant to the antimicrobial coating. Additionally, the invention relates to a kit that contains compositions of the antimicrobial agent and the non-pathogenic bacterium that are applied to the medical device before implantation in the mammal. Furthermore, this invention relates to a method for preventing a urinary tract infection comprising the use of an antimicrobial agent and a non-pathogenic bacterium.

BACKGROUND OF INVENTION

Indwelling vascular and urinary catheters are becoming essential in the management of hospitalized patients. Implanted orthopedic devices are also becoming more prevalent, partly to meet the needs of a growing elderly population. The benefit derived from these catheters and orthopedic devices, as well as other types of medical devices is often offset by infectious complications.

The most common hospital-acquired infection is urinary tract infection (UTI). The majority of cases of UTI are associated with the use of urinary catheters, including transurethral foley, suprapubic and nephrostomy catheters. These urinary catheters are inserted in a variety of populations, including the elderly, stroke victims, spinal cord-injured patients, post-operative patients and those with obstructive uropathy. Despite adherence to sterile guidelines for the insertion and maintenance of urinary catheters, catheter-associated UTI continues to pose a major problem. For instance, it is estimated that almost one-quarter of hospitalized spinal cord-injured patients develop symptomatic UTI during their hospital course. Gram-negative bacilli account for almost 60-70%, enterococci for about 0.25% and *Candida* species for about 10% of cases of UTI.

Colonization of bacteria on the surfaces of the implant or other part of the device can produce serious patient problems, including the need to remove and/or replace the implanted device and to vigorously treat secondary infective conditions. A considerable amount of attention and study has been directed toward preventing such colonization by the use of antimicrobial agents, such as antibiotics, bound to the surface of the materials employed in such devices.

Various methods have previously been employed to contact or coat the surfaces of medical devices with an antimicrobial agent. For example, one method would be to flush the surfaces of the device with an antimicrobial containing solution. Generally, the flushing technique would require convenient access to the implantable device. For example, catheters are generally amenable to flushing with a solution of rifampin and minocycline or rifampin and novobiocin. For use in flushing solutions, the effective concentration of the antibiotic would range from about 1 to 10 mg/ml for minocycline, preferably about 2 mg/ml; 1 to 10 mg/ml for rifampin, preferably about 2 mg/ml; and 1 to 10 mg/ml for novobiocin, preferably about 2 mg/ml. The flushing solution would normally be composed of sterile water or sterile normal saline solutions.

A known method of coating the devices is to first apply or absorb to the surface of the medical device a layer of tridodecylmethyl ammonium chloride (TDMAC) surfactant followed by an antibiotic coating layer. For example, a medical device having a polymeric surface, such as polyethylene, silastic esaltomers, polytetrafluoroethylene or Dacron, can be soaked in a 5% by weight solution of TDMAC for 30 minutes at room temperature, air dried, and rinsed in water to remove excess TDMAC. Alternatively, TDMAC precoated vascular catheters are commercially available. The device carrying the absorbed TDMAC surfactant coating can then be incubated in an antibiotic solution for up to one hour or so, allowed to dry, then washed in sterile water to remove unbound antibiotic and stored in a sterile package until ready for implantation. In general, the antibiotic solution is composed of a concentration of 0.01 mg/ml to 60 mg/ml of each antibiotic in an aqueous pH 7.4-7.6 buffered solution, sterile water, or methanol. According to one method, an antibiotic solution of 60 mg of minocycline and 30 mg of rifampin per ml of solution is applied to the TDMAC coated catheter.

Another successful coating method is impregnation of an antimicrobial agent. The antimicrobial agent penetrates and is incorporated in the exposed surfaces. The antimicrobial composition is formed by dissolving an antimicrobial agent in an organic solvent, adding a penetrating agent, and adding an alkalinizing agent to the composition. The composition is heated to a temperature between 30° C. and 70° C. prior to applying to the medical device. See, e.g., U.S. Pat. No. 5,902,283 and U.S. Pat. No. 5,624,704.

A further method known to coat the surface of medical devices with antibiotics involves first coating the selected surfaces with benzalkonium chloride followed by ionic bonding of the antibiotic composition. See, e.g., Solomon, D. D. and Sherertz, R. J., *J. Controlled Release*, 6:343-352 (1987) and U.S. Pat. No. 4,442,133.

These and many other methods of coating medical devices with antibiotics appear in numerous patents and medical journal articles. Practice of the prior art coating methods results in a catheter or medical device wherein only the surface of the device is coated with an antibiotic. While the surface coated catheter does provide effective protection against bacteria initially, the effectiveness of the coating diminishes over time. During use of the medical device or catheter, the antimicrobials leach from the surface of the device into the surrounding environment. Over a period of time, the amount of antibiotics present on the surface decreases to a point where the protection against bacteria is no longer effective.

Previously there have been several approaches to prophylaxis of urinary tract infection in chronically catheter dependent patients. Antibacterial compounds applied at the urethral meatus, silver impregnated catheters, intravesical instillation of various chemicals and antimicrobial agents, such as methenamine, cranberry juice and ascorbic acid, have been used with mixed success at best. Prophylactic oral antibiotics may reduce the incidence of asymptomatic bacteriuria in patients on clean intermittent catheterization but do not reduce that of symptomatic infection. A prospective study found a higher incidence of symptomatic infection among patients who received prophylactic antibiotics. Furthermore, prolonged treatment with antimicrobial agents, creates drug resistant pathogens, breakthrough infections and disruption of the normal flora.

With the world wide emergence of increased antibiotic resistant agents, an interest has developed in the use of bacterial interference as a means to cope with this problem. In nature, bacteria interact with each other as they attempt to establish themselves and dominate their environment. Some of the interactions are synergistic, whereas others are antagonistic. It has been suggested that these antagonistic interactions, so-called bacterial interference, may act in the prevention of certain infectious diseases. Bacterial interference operates through several mechanisms, i.e., production of antagonistic substances, changes in the bacterial microenvironment, and reduction of needed nutritional substances. Typically, the therapeutic approach of using bacterial interference involves the implantation of low-virulence bacterial strains that are potentially capable of interfering with the colonization and infection of more virulent microorganisms.

In recent years, the use of *Lactobacillus* has been investigated as a possible treatment for UTI. It is well known that indigenous, non-pathogenic bacteria predominate on intestinal, vaginal and uro-epithelial cells and associated mucus in the health state, and that pathogenic organisms (such as bacteria, yeast and viruses) predominate in the stages leading to and during infections. Organisms such as *Escherichia coli*, enterococci, *Candida, Gardnerella* and *Klebsiella* originate from the bowel, colonize the perineum, vagina, urethra and can infect the bladder and vagina. See e.g., U.S. Pat. No. 5,645,830 and U.S. Pat. No. 6,004,551.

In addition to the increased risk of infection associated with the use of urinary catheters, these patients are subjected to an increase in medical expenses. Typically, urinary catheters are replaced every 2-4 weeks. This time frame was established by the medical community based upon the safety concern of a biofilm of pathogenic bacteria developing on the catheter surface. Thus, patients may need to schedule an appointment every 2-4 weeks to have the catheter replaced resulting in the expense of office visits and the cost of approximately 24 catheters per year.

There is a general appreciation in the medical community that better methods to prevent the development of urinary catheter-associated UTI are needed. This invention describes for the first time the use of a non-pathogenic bacterium in combination with an antimicrobial agent to prevent UTI. It is noteworthy that the non-pathogenic bacterium used in this invention had been previously considered a pathogenic bacterium that results in UTI, thus suggesting, that this invention is indeed non-obvious.

Furthermore, this invention addresses the long-felt need of reducing the medical expenses incurred by patients that require a urinary catheter. Coating a urinary catheter with both an antimicrobial agent and a non-pathogenic bacterium will prolong the time frame between replacements of catheters. This invention could potentially increase the time from 2-4 weeks up to several months, thus, the amount of catheters and incurred medical expenses are reduced.

SUMMARY OF THE INVENTION

An embodiment of the present invention is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a non-pathogenic bacterial coating layer, wherein said non-pathogenic bacterial coating layer comprises a non-pathogenic gram-negative bacterium in an effective concentration to inhibit the growth of pathogenic bacterial and fungal organisms, wherein said non-pathogenic gram-negative bacterium is resistant to said antimicrobial agent.

In specific embodiments, the antimicrobial agent is selected from the group consisting of an antibiotic, an antiseptic, a disinfectant and a combination thereof. The present invention also encompasses lipid and other complex formulations of antimicrobial agents or derivatives thereof.

Another specific embodiment is that the antimicrobial agent is selected from the group of antibiotics consisting of penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

A further embodiment of the present invention is that the antimicrobial agent is selected from the group of antiseptics consisting of α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts.

In specific embodiments of the present invention, the non-pathogenic gram-negative bacterium is selected from the group consisting of Enterobacteriacea, *Pseudomonas aeruginosa, Stenotrophomonas maltophilia, Burkholderia cepacia, Gardnerella vaginalis*, and *Acinetobacter* species.

A specific embodiment is that the non-pathogenic gram-negative bacterium is *Pseudomonas aeruginosa*.

Another embodiment of the present invention is that the non-pathogenic gram-negative bacterium is selected from the group of Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*.

In a specific embodiment, the Enterobacteriacea is *Escherichia coli* 83972 (*E. coli* 83972) or mutants thereof.

In a further embodiment of the present invention, the non-pathogenic gram-negative bacterium is a bacterium which adheres to urinary catheters selected from the group consisting of *Providencia, Proteus, Pseudomonas aeruginosa, Escherichia coli*, and other urinary organisms.

A further embodiment is that the non-pathogenic bacterial coating layer further comprises viable whole cells of the non-pathogenic gram-negative bacterium.

Another embodiment is that the non-pathogenic bacterial coating layer further comprises non-viable whole cells or cellular structures or extracts of the non-pathogenic gram-negative bacterium.

In a further embodiment, the non-pathogenic bacterial coating layer further comprises at least one or more viable whole cells, non-viable whole cells or cellular structures or extracts of the non-pathogenic gram-negative bacterium.

Another embodiment of the present invention is that the non-pathogenic bacterial coating layer further comprises at least two non-pathogenic gram-negative bacteria.

An embodiment of the present invention is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a non-pathogenic bacterial coating layer, wherein said nonpathogenic bacterial coating layer comprises non-pathogenic gram-positive bacterium in an effective concentration to inhibit the growth of pathogenic bacterial and fungal organisms, wherein said non-pathogenic gram-positive bacterium is resistant to said antimicrobial agent.

In specific embodiments, the non-pathogenic gram-positive bacterium is selected from the group consisting of *Staphylococcus aureus*, coagulase-negative staphylococci, streptococci, enterococci, corynebacteria, and *Bacillus* species.

In another specific embodiment, the antimicrobial agent is selected from the group of antibiotics consisting of penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

A further embodiment of the present invention is that the non-pathogenic bacterial coating layer further comprises viable whole cell of the non-pathogenic gram-positive bacterium.

Another specific embodiment is that the non-pathogenic bacterial coating layer further comprises non-viable whole cells or cellular structures or extracts of the non-pathogenic gram-positive bacterium.

In specific embodiments, the non-pathogenic bacterial coating layer further comprises at least one or more viable whole cells, non-viable whole cells or cellular structures or extracts of the non-pathogenic gram-positive bacterium.

In a further embodiment, the non-pathogenic bacterial coating layer further comprises at least two non-pathogenic gram-positive bacteria.

Another specific embodiment is that the non-pathogenic bacterial coating layer further comprises at least one non-pathogenic gram-positive bacterium and at least one non-pathogenic gram-negative bacterium.

Another embodiment of the present invention is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a fungal coating layer, wherein said fungal coating layer comprises a fungus in an effective concentration to inhibit the growth of pathogenic bacterial and fungal organisms, wherein said fungus is resistant to said antimicrobial agent. A specific embodiment is that the fungus is *Candida*.

A further embodiment of the present invention is a method for preventing a urinary tract infection comprising the steps of pre-treating a patient with antibiotics for five to seven days; inoculating said patient with a culture of non-pathogenic bacterium; and applying to at least a portion of the surface of a urinary catheter, an antimicrobial coating layer having an antimicrobial agent in an effective concentration to inhibit the growth of bacterial and fungal organisms relative to uncoated medical devices.

A specific embodiment of the present invention is a kit comprising compositions to coat the surfaces of medical devices prior to implantation into a mammal comprising an antimicrobial agent and a culture from a non-pathogenic bacterium, wherein said non-pathogenic bacterium has been genetically modified to enhance the adherence of the bacterium to the implant surface. In a further embodiment of the kit, the compositions are in the same container. In another embodiment of the kit, the compositions are in different containers.

Another specific embodiment of the present invention is a kit comprising compositions to coat the surfaces of medical devices prior to implantation into a mammal comprising an antimicrobial agent and a culture from a non-pathogenic bacterium, wherein said non-pathogenic bacterium has been genetically modified to the decrease the sensitivity of the bacterium to antimicrobial agents.

A further embodiment is a kit comprising compositions to coat the surfaces of medical devices prior to implantation into a mammal comprising an antimicrobial agent and a culture from a non-pathogenic bacterium, wherein said non-pathogenic bacterium has been genetically modified to increase the stability of the bacterium at room temperature.

Another embodiment of the present invention is a kit comprising compositions to coat the surfaces of medical devices prior to implantation into a mammal comprising an antimicrobial agent and a culture from a non-pathogenic bacterium, wherein said non-pathogenic bacterium has been lyophilized and reconstituted prior to application to the surface of the implant.

Yet further, another embodiment of the present invention is a kit comprising a medical device pre-coated with an antimicrobial agent and compositions to coat said medical device prior to implantation into a mammal comprising a culture from a non-pathogenic bacterium.

Other and further objects, features and advantages would be apparent and eventually more readily understood by reading the following specification and or any examples of the present preferred embodiments of the invention are given for the purpose of the disclosure.

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one. As used herein "another" may mean at least a second or more.

The term "antiseptics" as used herein is defined as an antimicrobial substance that inhibits the action of microorganisms, including but not limited to α-terpineol, methylisothiazolone, cetylpyridinium chloride, chloroxylenol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts.

One skilled in the art is cognizant that these antiseptics can be used in combinations of two or more to obtain a synergistic effect. Furthermore, the antiseptics are dispersed along the surface of the medical device.

Some examples of combinations of antiseptics include a mixture of chlorhexidine, chlorhexidine and chloroxylenol, chlorhexidine and methylisothiazolone, chlorhexidine and α-terpineol, methylisothiazolone and α-terpineol; thymol and chloroxylenol; chlorhexidine and cetylpyridinium chloride; or chlorhexidine, methylisothiazolone and thymol. These combinations provide a broad spectrum of activity against a wide variety of organisms.

The term "antibiotics" as used herein is defined as a substance that inhibits the growth of microorganisms without damage to the host. For example, the antibiotic may inhibit cell wall synthesis, protein synthesis, nucleic acid synthesis, or alter cell membrane function.

Classes of antibiotics that can possibly be used include, but are not limited to, macrolides (i.e., erythromycin), penicillins (i.e., nafcillin), cephalosporins (i.e., cefazolin), carbepenems (i.e., imipenem, aztreonam), other beta-lactam antibiotics, beta-lactam inhibitors (i.e., sulbactam), oxalines (i.e. linezolid), aminoglycosides (i.e., gentamicin), chloramphenicol, sufonamides (i.e., sulfamethoxazole), glycopeptides (i.e., vancomycin), quinolones (i.e., ciprofloxacin), tetracyclines (i.e., minocycline), fusidic acid, trimethoprim, metronidazole, clindamycin, mupirocin, rifamycins (i.e., rifampin), streptogramins (i.e., quinupristin and dalfopristin) lipoprotein (i.e., daptomycin), polyenes (i.e., amphotericin B), azoles (i.e., fluconazole), and echinocandins (i.e., caspofungin acetate).

Examples of specific antibiotics that can be used include, but are not limited to, erythromycin, nafcillin, cefazolin, imipenem, aztreonam, gentamicin, sulfamethoxazole, vancomycin, ciprofloxacin, trimethoprim, rifampin, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, gatifloxacin, moxifloxacin, gemifloxacin, enoxacin, fleroxacin, minocycline, linezolid, temafloxacin, tosufloxacin, clinafloxacin, sulbactam, clavulanic acid, amphotericin B, fluconazole, itraconazole, ketoconazole, and nystatin. Other examples of antibiotics, such as those listed in Sakamoto et al, U.S. Pat. No. 4,642,104 herein incorporated by reference will readily suggest themselves to those of ordinary skill in the art.

The term "bacterial interference" as used herein is defined as an antagonistic interactions among bacteria to establish themselves and dominate their environment. Bacterial interference operates through several mechanisms, i.e., production of antagonistic substances, changes in the bacterial microenvironment, and reduction of needed nutritional substances.

The term "coating" as used herein is defined as a layer of material covering a medical device. The coating can be applied to the surface or impregnated within the material of the implant.

The term "effective concentration" means that a sufficient amount of the antimicrobial agent is added to decrease, prevent or inhibit the growth of bacterial and/or fungal organisms. The amount will vary for each compound and upon known factors such as pharmaceutical characteristics; the type of medical device; age, sex, health and weight of the recipient; and the use and length of use. It is within the skilled artisan's ability to relatively easily determine an effective concentration for each compound.

The term "gram-negative bacteria" or "gram-negative bacterium" as used herein is defined as bacteria which have been classified by the Gram stain as having a red stain. Gram-negative bacteria have thin walled cell membranes consisting of a single layer of peptidoglycan and an outer layer of lipopolysacchacide, lipoprotein, and phospholipid. Exemplary organisms include, but are not limited to, Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*. Other exemplary gram-negative organisms not in the family Enterobacteriacea include, but are not limited to, *Pseudomonas aeruginosa, Stenotrophomonas maltophilia, Burkholderia, Cepacia, Gardenerella, Vaginalis*, and *Acinetobacter* species.

The term "gram-positive bacteria" or "gram-positive bacterium" as used herein refers to bacteria, which have been classified using the Gram stain as having a blue stain. Gram-positive bacteria have a thick cell membrane consisting of multiple layers of peptidoglycan and an outside layer of teichoic acid. Exemplary organisms include, but are not limited to, *Staphylococcus aureus*, coagulase-negative staphylococci, streptococci, enterococci, corynebacteria, and *Bacillus* species.

The term "medical device" as used herein refers to any material, natural or artificial that is inserted into a mammal. Particular medical devices especially suited for application of the antimicrobial combinations of this invention include, but are not limited to, peripherally insertable central venous catheters, dialysis catheters, long term tunneled central venous catheters, long term non-tunneled central venous catheters, peripheral venous catheters, short-term central venous catheters, arterial catheters, pulmonary artery Swan-Ganz catheters, urinary catheters, artificial urinary sphincters, long term urinary devices, urinary dilators, urinary stents, other urinary devices, tissue bonding urinary devices, penile prostheses, vascular grafts, vascular catheter ports, vascular dilators, extravascular dilators, vascular stents, extravascular stents, wound drain tubes, hydrocephalus shunts, ventricular catheters, peritoneal catheters, pacemaker systems, small or temporary joint replacements, heart valves, cardiac assist devices and the like and bone prosthesis, joint prosthesis and dental prosthesis.

The term "mutant" as defined herein refers to a bacterium that has been mutated using standard mutagenesis techniques such as site-directed mutagenesis. One skilled in the art recognizes that the term mutant includes, but is not limited to base changes, truncations, deletions or insertions of the wild-type bacterium. Thus, the size of the mutant bacterium may be larger or smaller than the wild-type or native bacterium. Yet further, one skilled in the art realizes that the term mutant also includes different strains of bacteria or bacteria that has been chemically or physically modified as used herein.

The term "non-pathogenic bacteria" or "non-pathogenic bacterium" includes all known and unknown non-pathogenic bacterium (gram positive or gram negative) and any pathogenic bacteria that has been mutated or converted to a non-pathogenic bacterium. Furthermore, a skilled artisan recognizes that some bacteria may be pathogenic to specific species and non-pathogenic to other species; thus, these bacteria can be utilized in the species in which it is non-pathogenic or mutated so that it is non-pathogenic.

One specific embodiment of the present invention is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a non-pathogenic bacterial coating layer, wherein said non-pathogenic bacterial coating layer comprises a non-pathogenic gram-negative bacterium in an effective concentration to inhibit the growth of pathogenic bacterial and fungal organisms, wherein said non-pathogenic gram-negative bacterium is resistant to said antimicrobial agent.

The medical devices that are amenable to impregnation by the antimicrobial combinations are generally comprised of a non-metallic material such as thermoplastic or polymeric materials. Examples of such materials are rubber, plastic, polyethylene, polyurethane, silicone, Gortex (polytetrafluoroethylene), Dacron (polyethylene tetraphthalate), polyvinyl chloride, Teflon (polytetrafluoroethylene), latex, elastomers, nylon and Dacron sealed with gelatin, collagen or albumin.

The amount of each antimicrobial agent used to coat the medical device varies to some extent, but is at least a sufficient amount to form an effective concentration to inhibit the growth of bacterial and fungal organisms.

The antimicrobial agents can be used alone or in combination of two or more of them. The antimicrobial agents are dispersed throughout the surface of the medical device. The amount of each antimicrobial agent used to impregnate the medical device varies to some extent, but is at least of an effective concentration to inhibit the growth of bacterial and fungal organisms.

The antimicrobial agent and the non-pathogenic bacteria can be applied to the medical device in a variety of methods. Exemplary application methods include, but are not limited to, spraying, painting, dipping, sponging, atomizing, smearing, impregnating and spreading.

A skilled artisan is cognizant that the development of microorganisms in culture media is dependent upon a number of very important factors, e.g., the proper nutrients must be available; oxygen or other gases must be available as required; a certain degree of moisture is necessary; the media must be of the proper reaction; proper temperature relations must prevail; the media must be sterile; and contamination must be prevented.

A satisfactory microbiological culture contains available sources of hydrogen donors and acceptors, carbon, nitrogen, sulfur, phosphorus, inorganic salts, and, in certain cases, vitamins or other growth promoting substances. The addition of peptone provides a readily available source of nitrogen and carbon. Furthermore, different media results in different growth rates and different stationary phase densities. A rich media results in a short doubling time and higher cell density at a stationary phase. Minimal media results in slow growth and low final cell densities. Efficient agitation and aeration increases final cell densities. A skilled artisan will be able to determine which type of media is best suited to culture a specific type of microorganism. For example, since 1927, the DIFCO manual has been used in the art as a guide for culture media and nutritive agents for microbiology.

The method of the present invention preferably comprises a single step of applying an antimicrobial composition to the surfaces of a medical device and a single step of applying a non-pathogenic bacterium to the surfaces of a medical device. However, it is expected that several applications of the antimicrobial agent and/or non-pathogenic bacterium, or other substances, can be applied to the surface of the implant without affecting the adherence of the antimicrobial agent or the non-pathogenic bacterium. Furthermore, one skilled in the art is cognizant that the antimicrobial agent and the non-pathogenic bacterium can be applied together in a single step. Thus, the method of the application of the antimicrobial agent and the non-pathogenic bacterium can vary and should not be limited to the described methods. Furthermore, a skilled artisan recognizes that the order of the application of the compositions (i.e., antimicrobial agent and non-pathogenic bacterium) is not relevant and can vary for any given application to a medical device.

In specific embodiments, the antimicrobial agent is selected from the group consisting of an antibiotic, an antiseptic, a disinfectant and a combination thereof. More specifically, the antimicrobial agent is selected from the group of antibiotics consisting of penicillins, penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

In further specific embodiments, the antimicrobial agent is selected from the group of antiseptics consisting of α-terpineol, methylisothiazolone, cetylpyridinium chloride, chloroxyleneol, hexachlorophene, cationic biguanides, methylene chloride, iodine and iodophores, triclosan, nitrofurantoin, methenamine, aldehydes, azylic acid, silver, and benzyl peroxide.

Another embodiment of the present invention is that the non-pathogenic gram-negative bacterium is selected from the group consisting of Enterobacteriacea, *Pseudomonas aeruginosa*, *Stenotrophomonas maltophilia*, *Burkholderia cepacia*, *Gardnerella vaginalis*, and *Acinetobacter* species. In a specific embodiment, the non-pathogenic gram-negative bacterium is *Pseudomonas aeruginosa*.

In specific embodiments, the non-pathogenic gram-negative bacterium is selected from the group of Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*.

More specifically, the Enterobacteriacea is *Escherichia coli* 83972 or mutants thereof. *E. coli* 83972 (or, Knt, H) was originally isolated from a young woman as an asymptomatic bacteruria associated isolate. It expressed none of the adherence phenotype associated with uropathogenic *E. coli*. Preliminary studies suggested that *E. coli* 83972 possessed genes associated with type 1 (fim) but not P (pap) pili. However, a more recent analysis revealed that it possessed genes for type I and P pili synthesis (although it does not appear to express the P pili in vivo) as well as gene sequences homologous with foc (type 1C pili) and uca (G pili) genes.

Another specific embodiment of the present invention, is that the non-pathogenic gram-negative bacterium is a bacterium which adheres to urinary catheters selected from the group consisting of *Providencia, Proteus, Pseudomonas aeruginosa* and *Escherichia coli*.

In further embodiments of the present invention, the non-pathogenic bacterial coating layer further comprises viable whole cells of the non-pathogenic gram-negative bacterium. In addition to the use of viable whole cells, the non-pathogenic bacterial coating layer further comprises non-viable whole cells or cellular structures or extracts of the non-pathogenic gram-negative bacterium. In a specific embodiment, the non-pathogenic bacterial coating layer further comprises at least one or more viable whole cells, non-viable whole cells or cellular structures or extracts of the non-pathogenic gram-negative bacterium. Furthermore, the non-pathogenic bacterial coating layer further comprises at least two non-pathogenic gram-negative bacteria.

Furthermore, one skilled in the art is cognizant that the factor or factors which are responsible for the inhibition of the pathogens may be isolated and utilized, thus eliminating the necessity of using viable whole cells, non-viable whole cells or cellular structures or extracts. These inhibitory substances may be readily separated from cultured bacterial cells by techniques such as filtration, precipitation and centrifugation, which are readily known in the art.

A specific embodiment of the present invention is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a non-pathogenic bacterial coating layer, wherein said non-pathogenic bacterial coating layer comprises a non-pathogenic gram-positive bacterium in an effective concentration to inhibit the growth of pathogenic bacterial and fungal organisms, wherein said non-pathogenic gram-positive bacterium is resistant to said antimicrobial agent.

In specific embodiments of the present invention, the non-pathogenic gram-positive bacterium is selected from the group consisting of *Staphylococcus aureus*, coagulase-negative staphylococci, streptococci, enterococci, corynebacteria, and *Bacillus* species.

Another specific embodiment of the present inventions is that the antimicrobial agent is selected from the group of antibiotics consisting of penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

In specific embodiments of the present invention, the non-pathogenic bacterial coating layer further comprises viable whole cells of the non-pathogenic gram-positive bacterium. In addition, the non-pathogenic bacterial coating layer further comprises non-viable whole cells or cellular structures or extracts of the non-pathogenic gram-positive bacterium. In further embodiments, the non-pathogenic bacterial coating layer further comprises at least one or more viable whole cells, non-viable whole cells or cellular structures or extracts of the non-pathogenic gram-positive bacterium.

In specific embodiments, the non-pathogenic bacterial coating layer further comprises at least two non-pathogenic gram-positive bacteria. Another specific embodiment includes that the non-pathogenic bacterial coating layer further comprises at least one non-pathogenic gram-positive bacterium and at least one non-pathogenic gram-negative bacterium.

Another specific embodiment is a method for coating a medical device comprising the steps of applying to at least a portion of the surface of said medical device, an antimicrobial coating layer, wherein said antimicrobial coating layer comprises an antimicrobial agent in an effective concentration to inhibit the growth of bacterial and fungal organisms relative to uncoated medical devices; and applying to at least a portion of the surface of said medical device, a fungal coating layer, wherein said fungal coating layer comprises a fungus in an effective concentration to inhibit the growth of pathogenic bacterial and fungal organisms, wherein said fungus is resistant to said antimicrobial agent. More specifically, the fungus is *Candida*.

One specific embodiment of the present invention is a method for preventing a urinary tract infection comprising the steps of pretreating a patient with antibiotics for five to seven days; inoculating the patient with a culture of a non-pathogenic bacterium; and applying to at least a portion of the surface of a urinary catheter, an antimicrobial coating layer having an antimicrobial agent in an effective concentration to inhibit the growth of bacterial and fungal organisms relative to uncoated medical devices.

Another specific embodiment of the present invention is a kit comprising compositions to coat the surfaces of medical devices prior to implantation into a mammal comprising an antimicrobial agent and a culture from a non-pathogenic bacterium, wherein said non-pathogenic bacterium has been genetically modified to enhance the adherence of the bacterium to the implant surface. More specifically, the compositions are in the same container. Another embodiment includes the kit with the compositions in different containers.

The preferable mammal in the present invention is humans. However, other mammals may be used. Exemplary mammals include, but are not limited to, dogs, cats, cows, horses, rats, mice, monkeys, and rabbits.

One skilled in the art readily recognizes the significance of the development of a kit comprising the compositions to coat catheters prior to use in mammals. These kits may be readily prepared by utilizing standard bacterial culturing and storing techniques and standard preparations of antimicrobial solutions, which are readily known and applied in the art. The compositions used in the kit may be in the following forms, but are not limited to these forms, creams, capsules, gels, pastes, powders, liquids and particles.

It is also contemplated that a kit may comprise a medical device that has been pre-coated with an antimicrobial agent and compositions to coat the medical device prior to implantation into a mammal comprising a culture from a non-pathogenic bacterium. Thus, the medical staff only needs to apply the non-pathogenic bacterium composition to the medical device prior to implantation. One skilled in the art realizes that a kit containing a pre-coated medical device will reduce the amount of time that is needed for the implantation.

A further embodiment is a kit comprising compositions to coat the surfaces of medical devices prior to implantation into a mammal comprising an antimicrobial agent and a culture from a non-pathogenic bacterium, wherein said non-pathogenic bacterium has been genetically modified to decrease the sensitivity of the bacterium to antimicrobial agents. One skilled in the art is cognizant that mutations can be made to any given bacteria to alter the sensitivity to antimicrobial agents. Furthermore, a skilled artisan is well versed in the various methods to modify bacteria. For example, a standard modification is the insertion of an antibiotic resistant gene using transposons.

Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

Chemical mutagenesis. Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

Radiation Mutagenesis. The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Transposon mutagenesis. The genes in microorganisms are not static, but are capable under certain conditions to move around the genome. The process by which a gene moves from one place to another is transposition. If the transposon becomes inserted in a gene, then it usually results in the inactivation of the gene. Two transposons widely used for mutagenesis are Tn5, which confers neomycin and kanamycin resistance, and Tn10, which contains a marker for tetracycline resistance. Because the presence of the transposon itself can be followed by its antibiotic resistance properties, selection of antibiotic resistant cells after transposition is used to isolate a wide variety of mutants. Thus, transposon mutagenesis provides a useful tool for creating mutants throughout the chromosome.

One skilled in the art is cognizant that this simple bacterial mutagenesis can be utilized to alter the antibiotic resistance of specific bacteria to decrease the sensitivity of the bacteria to the antimicrobial agent used in the present invention. Furthermore, a skilled artisan is cognizant that the present invention does not propose the addition of an exorbitant amount of antimicrobial resistance genes. The present invention proposes the use of one or a maximum of a few anitmicrobial resistance genes, which are typically present in the bacteria which constitute the normal flora. The use of a non-pathogenic bacterium that is resistant to one or a maximum of few antimicrobial agents does not pose additional risks to the patient because 1) non-pathogenic bacterium is intended to prevent infection by the typically more resistant pathogenic bacterium; 2) the non-pathogenic bacterium should not cause symptomatic infections which require antibiotic therapy; and 3) the non pathogenic bacterium is typically made resistant to antimicrobial agents that are not usually used to treat established infection.

One specific embodiment is a kit comprising compositions to coat the surfaces of medical devices prior to implantation into a mammal comprising an antimicrobial agent and a culture from a non-pathogenic bacterium, wherein said non-pathogenic bacterium has been genetically modified to increase the stability of the bacterium at room temperature. Standard methods that are well-established in the art can be utilized to modify the bacteria, i.e., bacterial mutagenesis.

Another specific embodiment is a kit comprising compositions to coat the surfaces of medical devices prior to implantation into a mammal comprising an antimicrobial agent and a culture from a non-pathogenic bacterium, wherein said non-pathogenic bacterium has been lyophilized and reconstituted prior to application to the surface of the implant. A skilled artisan is cognizant that lyophilization of bacteria are standard techniques used in microbiology to increase the stability and preserve the microorganism indefinitely in a dried state.

Bacteria are lyophilized to increase the stability of the bacteria for long-term storage. Lyophilization stabilizes the formulation by removing the solvent component or components to levels that no longer support chemical reactions. This removal is accomplished by first freezing the formulation, thus separating the solutes from the solvent. Then the solvent is removed by primary drying or sublimation followed by a secondary drying or desorption. The formulation consists of three basic components—active ingredient, excipient, and solvent system. In general, the active ingredient in the pharmaceutical industry is defined by its potency and, in the diagnostic industry, by its reactivity. Depending on means of production, there may be variations in the composition of the active component from batch to batch.

Excipients serve several functions. They primarily provide a stable liquid environment for the active ingredient for some finite time. The excipient cryoprotects the active ingredient during the freezing process. In the freezing of formulations containing biological organisms, the formation of ice within leads to the organism's destruction by cell membrane rupture. Sucrose, glucose, and dextran are excipients used to cryoprotect organisms.

The excipient serves as a bulking agent. When solid concentrations of a formulation reach <2%, the resulting cake has poor structural qualities and leaves the container during the drying process. The addition of bulking agents such as mannitol and dextran strengthen cake structure. The role of the solvent system is often overlooked. Most formulations are totally aqueous solutions, although others contain solvents such as tertiary butyl alcohol to increase the solubility of some compounds. The solvent system is removed during drying, but its thermal properties have a major impact on the cosmetic properties of the final product.

Freezing and Drying the Formulation. Formation of ice during freezing results in dramatic changes in concentrations of the active ingredient and the excipient or excipients of the formulation.

In most formulations containing an active ingredient and an excipient, freezing greatly increases the concentration of the active ingredient and the excipient or excipients, but does not produce a well defined eutectic mixture. Instead, freezing produces a complex, glassy system that may be homogeneous or heterogeneous. This complex system, at this time, is produced in the interstitial region of ice crystals as a result of the freezing process.

Drying. For lyophilization to occur, the solvent is first removed by sublimation while the temperature of the frozen matrix is maintained below the eutectic (eutectic temperature is a point on a phase diagram where the temperature of the system or the concentration of the solution at the point cannot be altered without changing the number of phases present) or collapse temperature of the formulation. This is the primary drying process. The chamber pressure and product and shelf temperatures, during primary drying, are based on the formulation's eutectic or collapse temperature.

After primary drying, the residual moisture on the resulting cake surface is reduced to levels that no longer support biological growth and chemical reaction. This process is secondary drying. The reduction of moisture in the cake during secondary drying is accomplished by increasing the shelf temperature and reducing the partial pressure of water vapor in the container. The required partial pressure of water vapor and shelf temperature are ascertained from stability studies of lyophilized or vacuum-dried products having varied amounts of residual moisture.

The following examples are offered by way of example, and are not intended to limit the scope of the invention in any manner.

Example 1

Bacterial Interference

Patient selection. Patients were excluded with remediable etiologies for recurrent urinary tract infection, other than change in bladder management. Other exclusion criteria were existing urolithiasis, nephrostomy tube, ureteral stent, vesicoureteral reflux, immunosuppression, vascular or genitourinary prostheses, cardiovascular disease requiring antibiotic prophylaxis, on-going or anticipated need for antibiotic therapy for nonurological infection, pregnancy, fertility of female subjects not using some form of accepted birth control, age younger than 18 years or inability to give informed consent.

Symptomatic urinary tract infection was defined as the presence of bacteriuria (greater than $10^5$ CFU/ml) with fever, dysuria, increased urinary urgency, frequency or incontinence, flank, suprapublic or scrotal pain, exacerbation of baseline spasticity or autonomic dysreflexis, nausea and/or vomiting gross hematuria, coatovertebral or suprapubic tenderness, acrotal mass consistent with epididymitis or periurethral abscess, and/or a fluctant or exquisitely tender prostate. Significant laboratory values included white blood count greater than 10,500 cells per mm, and/or a left shift in the count and positive blood cultures, All patients discontinued all measures to suppress urinary tract infection for at least 2 weeks prior to the study, and all demonstrated a positive urine culture. No patient altered the form of bladder management during the study.

Inoculation protocol. Bacteria were stored frozen in 1% peptone per 30% glycerol solution at −80° C. Before patient inoculation, bacteria were grown overnight on agar plates and a single colony was inoculated into 30 ml nutrient extract broth. The culture was then incubated overnight at 37° C. with aeration. Bacteria were harvested by centrifugation and washed with 25 ml sterile irrigation saline and resuspended in irrigation saline at a final concentration of $10^5$ to $10^6$ CFU/ml.

At study entry, a urine culture was obtained. Each patient was treated as indicated with appropriate antibiotics for 5 to 7 days and any existing urinary catheter was changed 3 days after beginning therapy. The urine was recultured and the lower urinary tract was inoculated with E. coli 83972, 48 to 72 hours after completion of the antibiotic course. Inoculation consisted of instillation via a sterile bladder catheter of 30 ml. normal saline containing $10^5$ to $10^6$ colony-forming units per ml. Each inoculation cycle consisted of 2-3 inoculations on 3 consecutive days. Patients that were incontinent at low bladder volumes were treated with a Foley catheter balloon occluding the bladder neck or diversion stoma for 30 minutes after inoculation. If colonization was unsuccessful after 1 cycle of inoculations, the protocol was repeated up to 3 cycles.

For colonized patients, post-inoculation urine cultures and antibiotic susceptibilities were obtained weekly for 1 month, monthly for 1 year and quarterly thereafter. Successful stable colonization was defined as the presence of E. coli 83972 in the urine at detectable levels (greater than $10^3$ CFU/ml) for greater than 1 month after inoculation. E. coli isolated from urine were identified as E. coli 83972 using whole cell DNA fingerprint analysis. At each follow-up visit patients were queried about symptoms and signs of urinary tract infection, symptoms of extragenitourinary infection and the institution of antibiotic therapy since the preceding follow-up visit. Routine annual (more frequent if indicated) urological surveillance consisted of physical examination, serum creatinine determination, urinary tract imaging and urodynamic evaluation.

Long-term colonization. Persistent colonization (greater than 1 month) was achieved in 13 cases (Table 1). Mean duration of colonization was 12.3 months (range 2 to 40). The urine concentration of E. coli 83972 was maintained at greater than 105 CFU/ml. E. coli 83972 existed in pure culture (mean duration 4.6 months, range 1 to 13) or in the presence of contaminating organisms. Other bacterial genera were present as transient co-colonizers or persisted for longer intervals (mean 10.2 months, range 7 to 30) together with E. coli 83972. Co-colonizing bacteria, except for enterococcus, were present at reduced concentration of 0.1% of the concentration of E. coli 83972. When present, entereococci existed at the same concentration as E. coli 83972. In seven patients, E. coli 83972 was spontaneously eliminated from the bladder and replaced by other organisms. In five patients, E. coli 83972 was eliminated following antibiotic treatment for nongentiourinary infections.

TABLE 1

Duration of colonization and outcome in colonized subjects

| Pt. | Colonization Attempts | Colonization Duration (months) | Co-Colonizing Organisms* | Outcome |
|---|---|---|---|---|
| DLD | 1 | 2 | K. pneumoniae, group B Streptococcus | Spontaneous elimination |
| JDG | 1 | 5 | None | Treated for respiratory tract infection |
|  | 2 | 37 | K. pneumoniae, Enterococcus, P. aeruginosa | Lost to followup |
| JHK | 1 | 2 | Enterococcus, group B Streptococcus | Treated for respiratory tract infection |
|  | 2 | 40 | K. crytoca, Enterococcus† | Treated for toe infection |
| RA | 1 | 80 | K. pneumoniae, Enterococcus, S. aureus† | Spontaneous elimination |
|  | 2 | 16 | Enterococcus | Ongoing |
| RWR | 1 | 7 | Group B Streptococcus | Treated for toe infection |
|  | 2 | 26 | Group B Streptococcus, Marganella† | Ongoing |
| HK | 1 | 2 | None | Spontaneous elimination |
| EKM | 1 | 2 | K. pneumoniae, P. aeruginosa† | Treated for finger infection |
| TAK | 1 | 2 | Enterococcus | Spontaneous elimination |
|  | 2 | 14 | K. pneumoniae, group B Streptococcus | Ongoing |
| AM | 1 | 9 | None | Ongoing |
| RGR | 1 | 3 | Group B Streptococcus, Entercoccus† | Spontaneous elimination |
| HK | 1 | 16 | P. aeruginosa, Enterococcus† | Ongoing |
| RB | 1 | 6 | S. aureus | Spontaneous elimination |
| BR | 1 | 4 | P. aeruginosa, K. pneumoniae, Enterococcus† | Spontaneous elimination |

*Organism coexisted with E. coli 83972 greater than 3 months duration.
†Transient colonizations less than 3 months Patients had no symptomatic urinary tract infections while colonized with E. coli 83972 (0 infections per 18.4 patient-years). Successfully colonized patients had a mean of 3.1 urinary tract infections per year (range 2 to 7) before colonization. During the study 11 subjects had 1 or more infections. Symptomatic infection occurred in 4 subjects who were not successfully colonized with E. coli 83972 (Table 2). No correlation was found between other genitourinary or nongenitoumary related adverse events and bladder colonization with E. coli 83972.

TABLE 2

Adverse events

| Pt. | Genitourinary related | Nongenitourinary related |
|---|---|---|
| EAD | Urinary tract infection,* urinary tract infection* | Tooth abscess, upper respiratory tract infection |
| BJV | None | None |
| DLD | Mild incontinence | Impacted wisdom tooth |
| JDG | None | Upper respiratory tract infection, bronchitis, superficial cellulitis of scrotum, sinusitis |
| JHK | None | Upper respiratory tract infection, coccygeal decubitus, ingrown toe nail |
| RA | Suprapubic catheter occlusion | Sacral decubitus, topical antibiotic treatment |
| RWR | Urinary tract infection* | Toothache, muscle/chest pain, toe infection, growth of birthmark |
| BR | Urinary tract infection* | Diagnosis of diabetes mallitus, chronic back pain |
| EKM | Urinary tract infection* | Finger burn |
| TAK | Urinary tract infection*, urinary tract infection* | Flu, sore throat, toe infection, pneumonia |
| SS | Dysreflexia at inoculation | None |
| AM | None | Right arm cellulitis |
| RGR | Urethral discharge + urinary tract infection* | None |
| RK | None | Gastrointestinal evaluation, phantom pains |
| BB | Urosepsis* | Atrial fibrillation, warfarin toxicity, hyperglycemia |
| BR | Suprapubic catheter occlusion + hematuria, kidney cyst, cellulitis + pus at suprapubic catheter site, urinary tract infection* | Constipation, blood in stool, gastrointestinal evaluation, hemorrhoids, dizziness, panic attack on quinolone antibiotic |
| DM | Urinary tract infection* | Fall from gurney, hypokalemia |
| DNM | Urinary tract infection,* urinary tract infection* | Bilat. Hip pain |
| AWR | None | None |
| TJP | None | None |
| CB | Urinary tract infection* | None |

*Not while colonized with E. coli 83972.

Other methods of coating surfaces of medical devices with antibiotics are taught in U.S. Pat. No. 4,895,566 (a medical device substrate carrying a negatively charged group having a pKa of less than 6 and a cationic antibiotic bound to the negatively charged group); U.S. Pat. No. 4,917,686 (antibiotics are dissolved in a swelling agent which is absorbed into the matrix of the surface material of the medical device); U.S. Pat. No. 4,107,121 (constructing the medical device with ionogenic hydrogels, which thereafter absorb or ionically bind-antibiotics); U.S. Pat. No. 5,013,306 (laminating an antibiotic to a polymeric surface layer of a medical device); U.S. Pat. No. 5,902,283 (antimicrobial agents are impregnated in catheters) and U.S. Pat. No. 4,952,419 (applying a film of silicone oil to the surface of an implant and then contacting the silicone film bearing surface with antibiotic powders). One skilled in the art realizes that the above procedure can be modified, i.e., the length of time the implant is in the antimicrobial solution, the concentration of the antimicrobial agent and the drying time.

Example 2

Culturing of Microorgansims

Before inoculation or application of the bacteria to the catheter, the bacteria are grown utilizing the appropriate conditions as defined in the art. Typically, the bacteria are grown on an agar plate overnight at 37° C. A single colony is chosen from the overnight culture plate and is used to inoculate 30 ml of nutrient extract broth. The culture is incubated overnight at 37° C. with aeration. The bacteria are stored at room temperature or lyophilized for future use. If the bacteria are used immediately, then the bacteria are harvested by centrifugation and washed with sterile saline and resuspended in sterile saline at a final concentration of $10^5$ to $10^6$ CFU/ml.

Example 3

Bacterial Interference and Antimicrobial Coating

Three types of 1×1 cm square-shaped catheter material were tested: (1) uncoated latex catheter material; (2) latex catheter material coated with a "low concentration" of sulfamethoxazole (100 mg of sulfamethoxazole per ml of coating solution); and (3) latex catheter material coated with a "high concentration" of sulfamethoxazole (200 mg of sulfamethoxazole per ml of coating solution).

Two strains of pap-negative E. coli 83972 were tested: sulfamethoxazole-susceptible E. coli (strain HU2117), and sulfamethoxazole-resistant E. coli strain (HU2209).

Tested E. coli strains were grown overnight on L agar (HU2117) or L agar containing 100 micrograms per ml of sulfathiazole (HU2209) at 37° C., then inoculated into minimal media in screw cap tubes and incubated at 37° C. until the culture reached the early-log phase of growth. The culture was then diluted 1:100 into minimal media in a screw-cap tube which also contained a square of the catheter material. The catheter square was wedged into the tube approximately two centimeters below the surface of the liquid in a vertical position so that bacteria could not merely settle onto it. After 48 hours at 37° C., an aliquot of the culture was removed, diluted and plated onto L agar to determine the viable counts of the planktonic bacteria. The catheter squares were removed from the culture tubes aseptically and placed into 10 mls of buffered saline containing 0.01% SDS in snap-cap tubes. The tubes were vortexed briefly to wash the catheter square of remaining planktonic bacteria. Squares were removed aseptically and placed individually into standard glass scintillation vials containing 10 mls of buffered saline/SDS. The vials containing the squares were then subjected to 10 minutes of treatment in a sonic water bath. Following the treatment, which removes the attached bacteria from the membrane material, an aliquot was removed from each vial, diluted and plated onto L agar to determine the number of bacteria attached per square centimeter. A ratio of adherent bacteria to bacteria in the supernatant solution was determined (Table 3).

TABLE 3

Ratio of adherent bacteria to bacteria in the supernatant solution ($\times 10^{-7}$)

| E. coli Strain | Uncoated Latex | Latex coated with low conc. of Sulfamethoxazole | Latex coated with high conc. of Sulfamethoxazole |
|---|---|---|---|
| HU2117 (sulfa-susceptible) | 10.3 | 1.1 | 4.3 |
|  | 0.6 | 1.1 | 10 |
|  | 4.0 | 7.2 |  |
| Mean of observations: | 5.0 | 3.1 | 7.2 |
| HU2209 | 22 | 0.5 | 56 |

TABLE 3-continued

| | Ratio of adherent bacteria to bacteria in the supernatant solution (×10$^{-7}$) | | |
|---|---|---|---|
| E. coli Strain | Uncoated Latex | Latex coated with low conc. of Sulfamethoxazole | Latex coated with high conc. of Sulfamethoxazole |
| (sulfa-resistant) | 3.8 | 5.0 | 36 |
| Mean of observations: | 13 | 2.8 | 46 |

The sulfamethoxazole-resistant HU2209 *E. coli* strain tended to adhere better than the sulfamethoxazole-susceptible HU2117 *E. coli* strain to both uncoated latex catheter material (mean ratio of adherent bacteria to bacteria in the supernatant solution X 10$^{-7}$ of 13 vs. 5.0) and latex material coated with high concentration of sulfamethoxazole (mean ratio of adherent bacteria to bacteria in the supernatant solution X 10$^{-7}$ of 46 vs. 7.2). Thus, one skilled in the art realizes that the introduction of sulfamethoxazole resistance into *E. coli* does not reduce bacterial adherence to latex catheter material. This finding ensures that antimicrobial-resistant non-pathogenic strains of *E. coli* can avidly adhere to the surface of catheters.

The HU2117 sulfamethoxazole-susceptible *E. coli* strain tended to adhere less to latex coated with low concentration of sulfamethoxazole vs. uncoated latex material (mean ratio of adherent bacteria to bacteria in the supernatant solution X 10$^{-7}$ of 3.1 vs. 5.0). However, this trend for reduction in bacterial adherence to sulfamethoxazole-coated vs. uncoated latex could not be established when comparing adherence of the HU2117 sulfamethoxazole-susceptible *E. coli* strain to latex coated with high concentration of sulfamethoxazole vs. uncoated latex material (mean ratio of adherent bacteria to bacteria in the supernatant solution X 10$^{-7}$ of 7.2 vs. 5.0). Thus, a skilled artisan realizes that coating of latex catheter material with sulfamethoxazole may not consistently reduce bacterial adherence. This finding underscores the importance of assessing the potential impact of combining antimicrobial coating with another potentially protective measure, such as bacterial interference.

The HU2209 sulfamethoxazole-resistant *E. coli* strain adhered more to latex material coated with high concentration of sulfamethoxazole than to uncoated latex (mean ratio of adherent bacteria to bacteria in the supernatant solution X 10$^{-7}$ of 46 vs. 13). One skilled in the art realizes that the use of sulfamethoxazole-resistant strain of *E. coli* in combination with high concentration sulfamethoxazole-coated latex enhances bacterial adherence of this non-pathogenic strain. As a result, antimicrobial-resistant non-pathogenic strains persist in larger concentrations and for longer periods of time than antimicrobial-susceptible non-pathogenic strains on the surface of catheters. Thus, these results indicate that the use of a combination of bacterial interference plus antimicrobial coating has a higher efficacy than antimicrobial coating alone in preventing bacterial pathogens from colonizing the catheters resulting in an even lower likelihood of developing clinical catheter-related infections.

Example 4

Application of Antimicrobial Agent and Non-Pathogenic Bacterium and Use In Vivo

The urinary catheter is coated with an antimicrobial agent and a non-pathogenic bacterium. The non-pathogenic bacterium can be in a liquid composition or in a powdered composition. The powdered composition is derived from lyophilization. Both the antimicrobial agent and non-pathogenic bacterium are applied to the catheter and allowed to dry. After the antimicrobial agent and the non-pathogenic bacterium have been applied to the catheter, the coated catheter is then implanted into a patient similar to standard procedures. After implantation, the patients are followed and queried about symptoms and signs of urinary tract infections. The catheters are replaced at given times. The replaced catheters are also coated with the antimicrobial agent and the non-pathogenic bacterium.

One skilled in the art is cognizant that the urinary catheter treated with an antimicrobial agent and a non-pathogenic bacterium is potentially capable of withstanding the growth of a pathogenic biofilm longer than a non-treated catheter, thus increasing the time between catheter removal and exchange. The length of time necessary between removal of the catheters is determined by the strength of the antimicrobial agent and the non-pathogenic bacterium to inhibit the growth of pathogenic bacteria.

REFERENCES CITED

All patents and publications mentioned in the specification are indicative of the level of those skilled in the art to which the invention pertains. All patents and publications are herein incorporated by reference to the same extent as if each individual publication was specifically and individually indicated to be incorporated by reference.

Ditunno, J. F., Jr. and Farmal, C. S., N Engl J Med, 330: 550, 1994
Hackler, R. H., J Urol, 117: 486, 1977
Maynard, F. M. and Diakno, A. C. J Urol, 132: 943, 1984
Whiteneck, G. G. et al., Paraplegia, 30: 817, 1992
Cardenas, D. D. and Hooton, T. M. Arch Phys Med Rehabil, 76: 272, 1995
Waites, K. B., et al., J. Arch Phys Med Rehabil, 704: 691, 1993
Stover, S. L., et al., Arch Phys Med Rehabil, 70: 47, 1989
Stark, R. P. and Maki, D. G. N Engl J Med, 911: 560, 1984
Sotolange, J. R., Jr. and Knleilat, N. J Urol, 143: 979, 1990
Warren, J. W., Med Clin North Am, 75: 481, 1991
Hansson, S., et al:, BMJ, 298: 853, 1989
Hansson, S., et a.l, BMJ, 298: 856, 1989
Nicolle, L. E. Infect Dia Clin North Am, 11: 647, 1997
Reid, G., et al., Clin Microbiol Rev. 3: 335, 1990
Lindberg, U.: Acts Paediatr Scand, 64: 718, 1975
Anderson, P., et al., Infect Immun, 58: 2915, 1991
Agace, W. W., et al., J Clin Invest, 92: 780, 1999
Hull, R. A., et al., Infect Immun, 67: 429, 1999
Gouby, A., et al., J Clin Microbiol, 30: 1588, 1992
Castello, T., et al., Spinal Cord, 34: 592, 1996
Avorn, J., et al., JAMA, 271: 761, 1994
Banover, K., et al., J Am Paraplegia Soc. 14: 52, 1991
Johnson, J. R., et al., J Infect Dis. 182: 1145, 1990
Riley, D. K., et al., Am J Med, 88: 349, 1995
Mohler, J. L., et al., J Urol, 138: 336, 1987
Bakke, A. and Vollset, S. E.: J Urol, 148: 527, 1999
Wulit, B., et al., J Urol, 150: 2057, 1998

One skilled the art readily appreciates that the present invention is well adapted to carry out the objectives and obtain the ends and advantages mentioned as well as those inherent therein. Methods, procedures and techniques described herein are presently representative of the preferred embodiments and are intended to be exemplary and are not intended as limitations of the scope. Changes therein and other uses will occur to those skilled in the art which are encompassed within the spirit of the invention or defined by the scope of the pending claims.

We claim:

1. A method for preventing a urinary tract infection in a catheter dependent human patient comprising the steps of:
colonizing the patient with a culture of a gram-negative non-pathogenic Enterobacteriacea bacterium that is resistant to an antimicrobial agent; and
managing the patient's bladder by using a urinary catheter, wherein at least a portion of the surface of the urinary catheter is coated with an antimicrobial coating layer having the antimicrobial agent in an effective concentration to inhibit the growth of bacterial and fungal organisms relative to uncoated medical devices
whereby the bacterium and antimicrobial agent prevents the urinary tract infection in the catheter dependent patient.

2. The method of claim 1, wherein said antimicrobial agent is selected from the group consisting of an antibiotic, an antiseptic, a disinfectant and a combination thereof.

3. The method of claim 2, wherein said antimicrobial agent is selected from the group of antibiotics consisting of penicillins, cephalosporins, carbepenems, other beta-lactams antibiotics, aminoglycosides, macrolides, lincosamides, glycopeptides, tetracylines, chloramphenicol, quinolones, fucidins, sulfonamides, trimethoprims, rifamycins, oxalines, streptogramins, lipopeptides, ketolides, polyenes, azoles, and echinocandins.

4. The method of claim 2, wherein said antimicrobial agent is selected from the group of antiseptics consisting of α-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, silver, benzyl peroxide, alcohols, and carboxylic acids and salts.

5. The method of claim 1, wherein said gram-negative non-pathogenic Enterobacteriacea bacterium is a non-pathogenic strain of bacteria selected from the group of Enterobacteriacea consisting of *Escherichia, Shigella, Edwardsiella, Salmonella, Citrobacter, Klebsiella, Enterobacter, Hafnia, Serratia, Proteus, Morganella, Providencia, Yersinia, Erwinia, Buttlauxella, Cedecea, Ewingella, Kluyvera, Tatumella* and *Rahnella*.

6. The method of claim 5, wherein said Enterobacteriacea is *Escherichia coli* 83972 or mutants thereof.

7. The method of claim 1, wherein the colonizing step is performed simultaneously with the managing step.

8. The method of claim 7, wherein at least a portion of the surface of the urinary catheter is coated with the gram negative non-pathogenic bacterium.

9. A method of preventing a urinary tract infection in a catheter dependent patient comprising the step of inserting a urinary catheter into the patient wherein at least a portion of the surface of the urinary catheter is coated with an antimicrobial coating layer and a non-pathogenic bacterial coating layer having a gram-negative bacterium that is resistant to the antimicrobial agent whereby the antimicrobial layer and non-pathogenic bacterial layer prevents the urinary tract infection in the catheter dependent patient.

* * * * *